US006632242B2

(12) United States Patent
Igaki

(10) Patent No.: US 6,632,242 B2
(45) Date of Patent: Oct. 14, 2003

(54) STENT FOR VESSEL

(75) Inventor: Keiji Igaki, Shiga (JP)

(73) Assignee: Kabushikikaisha Igaki Iryo Sekkei, Shiga (JP)

( * ) Notice: Subject to any disclaimer, the term of this patent is extended or adjusted under 35 U.S.C. 154(b) by 0 days.

(21) Appl. No.: 09/795,858

(22) Filed: Feb. 28, 2001

(65) Prior Publication Data

US 2001/0032012 A1 Oct. 18, 2001

Related U.S. Application Data

(62) Division of application No. 09/194,262, filed as application No. PCT/JP98/01489 on Mar. 31, 1998, now Pat. No. 6,200,335.

(30) Foreign Application Priority Data

Mar. 31, 1997 (JP) ........................................... P9-078682

(51) Int. Cl.[7] ................................................. A61F 2/06
(52) U.S. Cl. ..................................................... 623/1.15
(58) Field of Search .............................. 623/1.13, 1.15, 623/1, 1.12, 1.14, 1.16–1.22, 1.3–1.32, 1.35, 1.36, 1.44, 1.49, 1.5–1.54

(56) References Cited

U.S. PATENT DOCUMENTS

| | | | | |
|---|---|---|---|---|
| 4,416,028 A | * | 11/1983 | Eriksson et al. | 623/1.38 |
| 5,366,504 A | * | 11/1994 | Andersen et al. | 606/194 |
| 5,591,222 A | * | 1/1997 | Susawa et al. | 606/195 |
| 5,741,325 A | * | 4/1998 | Chaikof et al. | 623/1.35 |
| 6,124,523 A | * | 9/2000 | Banas et al. | 606/191 |

FOREIGN PATENT DOCUMENTS

| | | | | |
|---|---|---|---|---|
| JP | 7-509152 | 10/1995 | | A61F/2/06 |
| JP | 8-196642 | 8/1996 | | A61M/29/00 |
| WO | WO-95/14500 | 6/1995 | | A61M/29/00 |

\* cited by examiner

*Primary Examiner*—Gary Jackson
*Assistant Examiner*—(Jackie) Tan-Uyen T. Ho
(74) *Attorney, Agent, or Firm*—Bell, Boyd & LLC

(57) ABSTRACT

A stent for a vessel inserted in use into the vessel of a living body including a tubular member constituting a passageway from one end to its opposite end. The tubular member includes a main mid portion and low tenacity portions formed integrally with both ends of the main mid portion. The low tenacity portions are lower in tenacity than the main mid portion. These low tenacity portions are formed so as to have the Young's modulus approximate to that of the vessel of the living body in which is inserted the stent, so that, when the stent is inserted into the vessel, it is possible to prevent stress concentrated portions from being produced in the vessel.

6 Claims, 4 Drawing Sheets

STENT FOR VESSEL

This is a divisional of application Ser. No. 09/194,262, filed Jan. 29, 1999, now U.S. Pat. No. 6,200,335 issued Mar. 13, 2001, which is a 371 of PCT/JP98/01489, filed Mar. 31, 1998, incorporated by reference.

TECHNICAL FIELD

This invention relates to a stent for a vessel loaded in a vessel, such as blood vessel, lymphoduct, bile duct or urinary duct. The stent for the vessel is used for holding a constant state of the configuration of the vessel when the stent is loaded in the vessel.

BACKGROUND ART

Heretofore, if a constricted portion is produced in the blood vessel, such as artery, a balloon forming portion annexed to near the distal end of a catheter is introduced into the constricted portion in the blood vessel to from a balloon to expand the constricted portion to improve the blood stream, by way of performing a percutaneous blood vessel forming technique (PTA).

Meanwhile, it is known that, if the PTA is applied, the portion which once suffered from constriction tends to undergo re-constriction with a high probability.

For preventing this re-constriction, it is practiced to apply a tubular stent in the portion of the vessel treated with PTA. This stent is buried in an expanded state in a blood vessel 2 as shown in FIG. 11 to support the blood vessel 2 from its inside to prevent occurrence of re-constriction in the blood vessel 2.

In clinical cases in which a stent prepared by weaving a linear material of stainless steel in a mesh is introduced in the portion of the vessel treated with PTA, reconstriction occurred in a probability of approximately 15%.

For prohibiting this re-constriction, there is proposed in Japanese Laying-open publication Hei-5-502179 (W091/01097) a stent prepared by polymer Meanwhile, blood re-constriction after loading the stent occurs in a majority of cases at a stent end or beginning from the stent end.

The stent used in the inserted state in the blood vessel holds the blood vessel in the expanded state, so that it is designed to have tenacity sufficiently higher than that of the blood vessel. For example, the blood vessel has a Young's modulus equal to approximately 3×10' pascal, whereas the stainless steel as a main material of the stent used for holding the blood vessel in the expanded state is approximately 3×10" pascal.

At this time, the blood vessel 2 is reduced in diameter at the portions in register with ends 1a, 1b of the stent 1 where the blood vessel 2 ceases to be supported by the stent 1. The portions of the blood vessel 2 supported by the ends 1a, 1b of the stent 1 represent stress-concentrated portions.

The blood vessel 2, especially the artery, perpetually performs pulsations to cause the blood to flow. The result is that the load due to the pulsations are repeatedly applied to the stress-concentrated portions of the blood vessel 2 supported by the ends 1a, 1b of the stent 1, so that the inner wall of the blood vessel 2 tends to be damaged by the ends 1a, 1b of the stent 1. Since the load is applied to the stress-concentrated portions of the blood vessel 2 supported by the ends 1a, 1b of the stent 1, there are produced injuries in the inner film or beginning from the inner filling to the outer filling of the blood vessel 2. If damaged, the blood vessel 2 recuperates the damaged portion as a reaction proper to a living body. In recuperating the damaged portion, the blood vessel 2 has its inner film multiplied excessively to cause the re-constriction.

DISCLOSURE OF THE INVENTION

It is therefore an object of the present invention to provide a novel stent for a vessel capable of eliminating the drawback of a conventional stent for the vessel.

It is another object of the present invention to provide a stent for a vessel which can positively prevent damages to the vessel whilst it positively keeps the vessel of a living body, such as a blood vessel, in an expanded state.

It is yet another object of the present invention to provide a stent for a vessel which can be inserted in position without producing stress-concentrated portions in the vessel.

For accomplishing the above object, the present invention provides a stent for a vessel, inserted in use into the vessel of a living body, including a tubular member constituting a passageway from one end to the opposite end thereof. The tubular member includes a main mid portion and low tenacity portions formed integrally with both ends of the main mid portion. The low tenacity portions is lower in tenacity than the main mid portion. The low tenacity portions are formed so as to have the Young's modulus approximate to that of the vessel of the living body into which is inserted the stent.

The low tenacity portions are formed by stretching both ends of the tubular member for reducing the thickness thereat.

The low tenacity portions may also be formed by setting the surface density of both ends of the tubular member so as to be lower than that at both ends of the tubular member having a defined value. If the tubular member is prepared by knitting or weaving a fine metal wire or a polymer yarn, the low tenacity portions are formed by lowering the density of the meshes of knitting or weaving on both ends of the tubular member.

The low tenacity portions may also be formed by forming both ends of the tubular member of a material lower in Young's modulus than the material making up the main mid portions.

If the tubular member is formed of the polymer material exhibiting biological absorptivity, the stent holds its shape for a few weeks to a few months after insertion into the blood vessel. However, it can vanish in about several months after insertion by absorption into the living tissue.

If the tubular member is formed by weaving or knitting a fine metal wire or a polymer yarn, the low tenacity portions can be formed on both ends of the tubular member by employing a soft linear material for these ends lower in strength than the linear material making up the main mid portion.

BEST MODE FOR CARRYING OUT THE INVENTION

Figure 1:
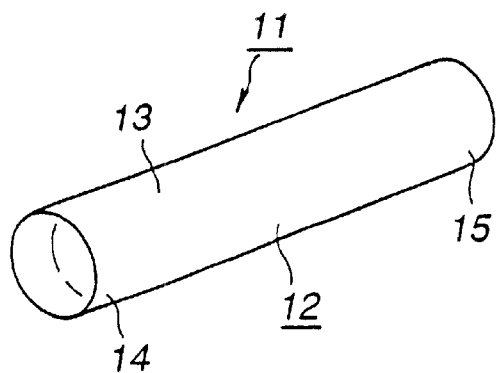
FIG. 1 is a perspective view showing a stent for a vessel according to the present invention.
Figure 2:
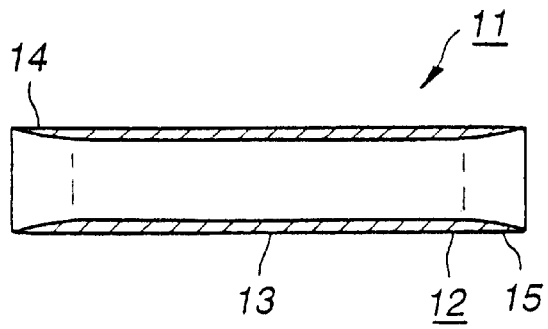
FIG. 2 is a cross-sectional view showing the stent for the vessel shown in FIG. 1.

Referring to the drawings, preferred embodiments of the present invention will be explained in detail.

A stent 11 for a vessel according to the present invention is used as it is inserted into a blood vessel, such as a coronary vessel, and includes a tubular member 12 providing a passageway beginning from its one end to its opposite end, as shown in FIG. 1. This tubular member 12 is formed of stainless steel having superior corrosion resistance and biological compatibility.

The metals making up the tubular member 12 may be enumerated by a nickel titanium alloy, platinum, tantalum and platinum, in addition to stainless steel.

The tubular member 12 has a main mid portion 13 having sufficient toughness to hold the blood vessel in the expanded state when the tubular member 12 is inserted into the blood vessel. On both sides of the main mid portion 13, there are integrally formed low tenacity portions 14, 15 lower in tenacity than the main mid portion 13. These low tenacity portions 14, 15 are formed by setting both ends of the tubular member 12 so as to be smaller in thickness than the main mid portion 13.

The low tenacity portions 14, 15, thus reduced in thickness, are formed by cutting off or forging both ends of the tubular member 12. At this time, the low tenacity portions 14, 15 are desirably formed so as to be progressively thinner in thickness from the main mid portion 13 to both ends of thicker thickness. That is, the tubular member 12 is formed with the low tenacity portions 14, 15 progressively lower in tenacity from the main mid portion 13 to both end portions.

The main mid portion 13 is designed to have a Young's modulus sufficiently larger than that of the blood vessel so that the blood vessel, into which is inserted the stent, will be kept in the expanded state. Since the blood vessel, into which is inserted the stent, has the Young's modulus approximately equal to $3 \times 10^7$ pascal, the main mid portion 13 is designed to have the Young's modulus approximately equal to $3 \times 10^{11}$. The low tenacity portions 14, 15 are formed so as to have a Young's modulus approximately equal to or slightly larger than that of the blood vessel.

Figure 3:
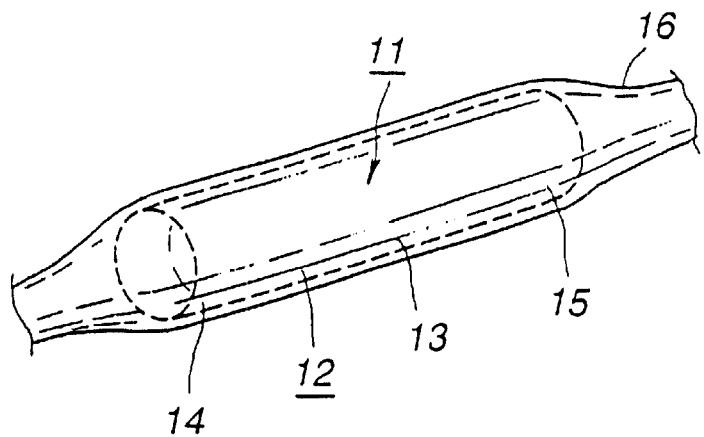
FIG. 3 is a perspective view showing the state in which the stent shown in FIG. 1 has been inserted into the blood vessel.

With the stent 11 having the main mid portion 13 of high tenacity, on both ends of which are formed the low tenacity portions 14, 15, as described above, the blood vessel 16 can be kept in the expanded state by the high tenacity main mid portion 13 when the stent 11 is inserted in the blood vessel 16, as shown in FIG. 3.

Figure 4:
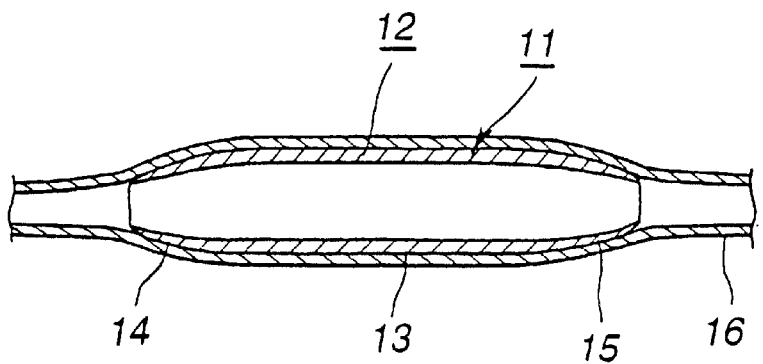
FIG. 4 is a cross-sectional view showing the state in which the stent shown in FIG. 1 has been inserted into the blood vessel which is undergoing pulsating movements.

The blood flows in the blood vessel 16 through the stent 11. Also, as the blood vessel 16 repeats expansion and contraction in diameter on pulsations, it applies a load to the stent 11 for reducing its diameter. At this time, the low tenacity portions 14, 15 formed on both ends of the tubular member 12 readily undergo elastic displacement due to the pulsations of the blood vessel 16, as shown in FIG. 4. That is, the low tenacity portions 14, 15 undergo elastic displacement gradually from the main mid portion 13 towards the ends of the tubular member 12 to prevent stress-concentrated portions from being produced in the blood vessel 16.

With the above-described stent 11 which, on insertion into the blood vessel 16, can prohibit generation of the stress-concentrated portions therein, it is possible to prevent damages to the blood vessel 16, and to suppress re-constriction ascribable to the recuperative function of the blood vessel 16.

Figure 5:
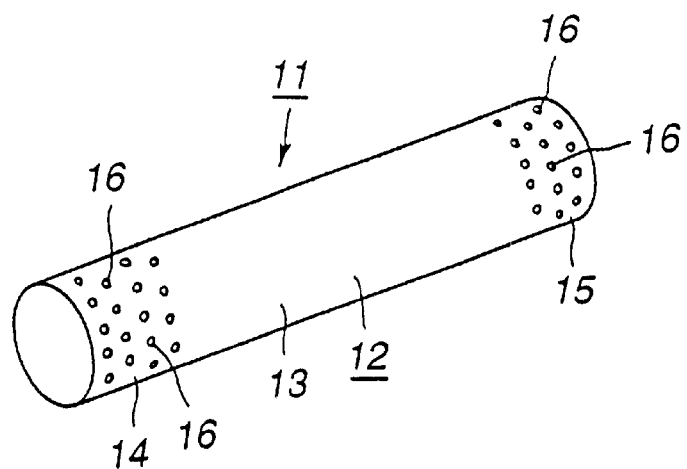
FIG. 5 is a perspective view showing another embodiment of a stent for a vessel according to the present invention.

By boring plural micro-sized through-holes 16 towards the ends of the tubular member 12 having a uniform wall thickness, as shown in FIG. 5, and by reducing the density of the ends of the tubular member 12 as compared to that at the main mid portion 13, the low tenacity portions 14, 15 lower in tenacity than the main mid portion 13 are formed at the ends of the tubular member 12. The number of the micro-sized through-holes 16 of the low tenacity portions 14, 15 is preferably increased progressively from the main mid portion 13 towards the ends of the tubular member 12. By boring the micro-sized through-holes 16, in this manner, the low tenacity portions 14, 15 are lowered in tenacity progressively from the main mid portion 13 towards the ends of the tubular member 12.

In addition, by boring the micro-sized through-holes 16 so as to be progressively larger in diameter from the main mid portion 13 towards the ends of the tubular member 12, the low tenacity portions 14, 15 may be progressively decreased in tenacity from the main mid portion 13 towards the ends of the tubular member 12.

Figure 6:
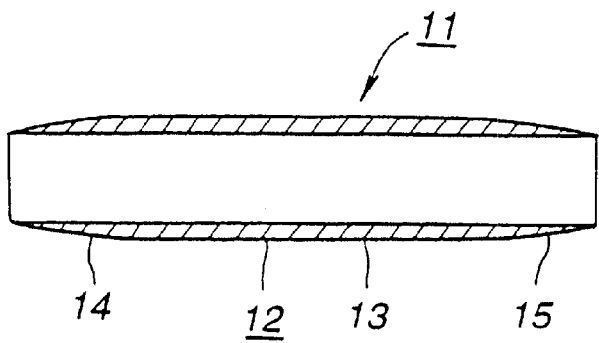
FIG. 6 is a perspective view showing yet another embodiment of a stent for a vessel according to the present invention in which low-tenacity portions at the ends of a tubular member are progressively reduced in diameter.

The low tenacity portions 14, 15 formed at the respective ends of the tubular member 12 are preferably reduced in diameter progressively from the main mid portion 13 towards the ends of the tubular member 12, as shown in FIG. 6. By this configuration of the tubular member 12, the portion of the blood vessel 16 expanded by the main mid portion 13 is progressively reduced in diameter to conform to the low tenacity portions 14, 15, decreasing in diameter, when the stent 11 is inserted into the blood vessel 16, thus more positively suppressing occurrence of the stress concentrated portions.

Although the stent 11 is formed of metal, such as stainless steel, it may also be formed of a polymer material.

Figure 7:
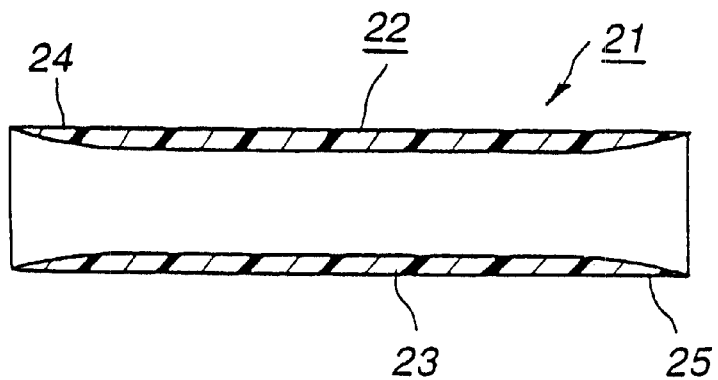
FIG. 7 is a cross-sectional view showing a stent for a vessel of the present invention in which the tubular member is formed of a polymer material.

A stent 21, formed of the polymer material, has a tubular member 22 which is molded from the polymer material using an injection molding method or an extrusion molding method, or which is a sheet of a polymer material wrapped into a tube, as shown in FIG. 7.

The polymer material of the tubular member 22 is selected so as to have biological compatibility and in particular biological absorptivity. The materials having the biological absorptivity may be enumerated by polylactic acid (PLA), polyglycolic acid (PGA), polyglactin (polyglycolic acid polylactic acid copolymer), polydioxanone, polyglyconate (trimethylene carbonate glycolide copolymer), and a copolymer of polyglycolic acid or polylactic acid E-caprolactone. The stent 11, formed of the polymer material exhibiting biological absorptivity, while holding its shape for a few weeks to a few months after insertion into the blood vessel, can vanish in about several months after insertion by absorption into the living tissue.

The tubular member 22 also has a main mid portion 23 exhibiting toughness sufficient to hold the blood vessel in an expanded state on absorption of the stent 21 into the blood vessel, as shown in FIG. 7. On both sides of the main mid portion 23 are integrally formed low tenacity portions 24, 25 lower in tenacity than the main mid portion 23. These low tenacity portions 24, 25 are formed by reducing the wall thickness of both ends of the tubular member 22 so as to be thinner than that of the main mid portion 13.

These thin-walled low tenacity portions 24, 25 are formed by stretching both ends of the tubular member 22.

In the stent 21 formed of the polymer material, similarly to the stent 11 of metal, described above, the low tenacity portions 24, 25 may be formed by boring micro-sized through-holes in both ends of the tubular member 22. Preferably, the low tenacity portions 24, 25 are progressively reduced in diameter from the main mid portion 23 towards the ends of the tubular member 22.

The stent according to the present invention may also be formed by weaving fine metal wires or polymer yarn.

Referring to the drawings, a stent 31 formed of the fine metal wires is explained.

Figure 8:
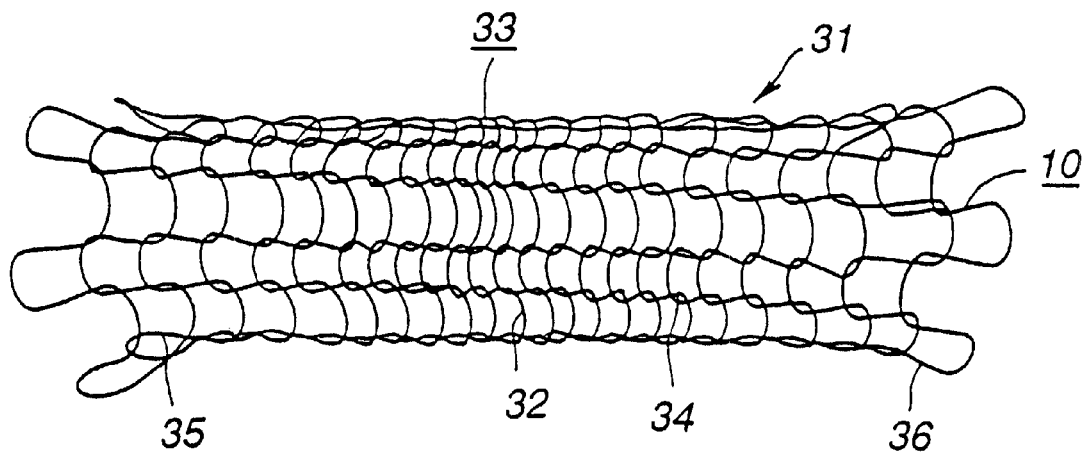
FIG. 8 is a perspective view showing a stent for a vessel of the present invention in which the tubular member is formed by weaving a fine metal wire or a polymer yarn.

The stent 31 includes a tubular member 33 formed by weaving fine wires 32 of metal exhibiting biological compatibility, such as stainless steel, nickel-titanium alloy, platinum, tantalum or platinum, as shown in FIG. 8. The tubular member 33 is formed by a number of meshes formed by knitting a sole fine metal wire 32 so as to form loops.

The tubular member 33 has a main mid portion 34 having tenacity sufficient to hold the blood vessel in an expanded state on insertion into the blood vessel. On both ends of the main mid portion 34 are integrally formed low tenacity portions 35, 36 lower in tenacity than the main mid portion 34. These low tenacity portions 35, 36 are formed by using a rougher pitch of the meshes than in the main mid portion 34 having a preset mesh density. At this time, the low tenacity portions 35, 36 are preferably knitted so as to be progressively lower in mesh density from the main mid portion 34 towards the ends of the tubular member 33.

It is noted that the main mid portion 34 is knitted so as to have meshes of such density sufficient to realize the Young's modulus sufficiently larger than that of the blood vessel to hold the blood vessel in an expanded state on insertion of the stent 31 in the blood vessel, while the low tenacity portions 35, 36 are knitted so as to have meshes of such density approximately equal to or slightly larger than that of the blood vessel.

Figure 9:
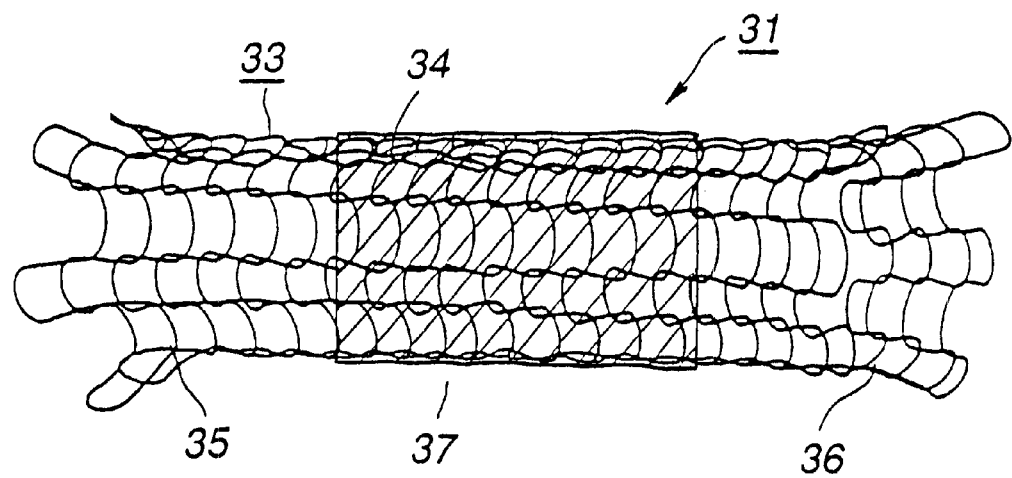
FIG. 9 is a perspective view showing a stent for a vessel of the present invention in which a reinforcement member is provided at a main mid portion of a tubular member formed by weaving a fine metal wire or a polymer yarn.

For forming the stent 31 having the low tenacity portions 35, 36 lower n tenacity than the main mid portion 34 towards the ends of the tubular member 33, a fine metal wire 32 is knitted to a density such that the tubular member 33 in its entirety has the Young's modulus approximately equal to or slightly larger than that of the blood vessel. The main mid portion 34 of the tubular member 33 is fitted with a reinforcement 37 formed of layered polymer material to increase toughness, at the portion 34, as shown in FIG. 9. The polymer materials, making up the reinforcement 37, are layered so as to have a tenacity sufficient to hold the blood vessel in the expanded state.

The reinforcement 37 is formed by outset-molding a polymer material on the tubular member 33 formed in turn by weaving the fine metal wire 32. That is, the reinforcement 37 is formed by injection molding a polymer material on the tubular member 33 placed in a metal mold.

For increasing tenacity of the main mid portion 34, a fine metal wire 32 may be woven in the main mid portion 34.

The stent 31, knitted as shown in FIG. 8, may also be formed using polymer yarn. These yarn are formed by spinning polymer fibers.

The stent 31, formed by the tubular member 33 knitted by biologically absorptive polymer fibers, hold the knitted state for a few weeks to a few months after insertion into the blood vessel. However, it can vanish on absorption into the living tissue in several months after insertion.

The biologically absorptive polymer may be enumerated by polylactic acid (PLA), polyglycolic acid (PGA), polyglactin (polyglycolic acid polylactic acid copolymer), polydioxanone, polyglyconate (trimethylene carbonate glycolide copolymer), and a copolymer of polyglycolic acid or polylactic acid E-caprolactone.

A variety of pharmaceuticals can be mixed into the yarn of polymer fibers. By mixing an- X-ray non-permeating agent into the yarn at the time of spinning the fibers, the state of the stent for the vessel, inserted into the blood vessel, can be observed by X-rays. It is also effective to mix thrombus dissolving agents or anti-thrombotic agents, such as heparin, urokinase or t-PA.

The above stent 31 is basically formed by knitting a sole fine metal wire or a sole polymer yarn of a substantially uniform thickness. However, by varying the thickness of the fine metal wire or the yarn, the tubular member 33 may be formed so as to have low tenacity portions 35, 36 at both ends thereof lower in tenacity than the main mid portion 34. Specifically, by forming the main mid portion 34 of the tubular member 33 by a thicker metal wire or yarn of higher toughness and by forming the ends of the tubular member 33 from a finer metal wire or yarn of a lower toughness than the metal wire or yarn of the main mid portion 34, the low tenacity portions 35, 36 may be formed on both ends of the tubular member 33.

Figure 10:
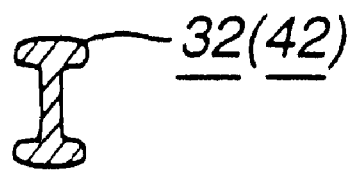
FIG. 10 is a cross-sectional view showing the fine metal wire or the polymer yarn constituting the main mid portion of the tubular member.
Figure 11:
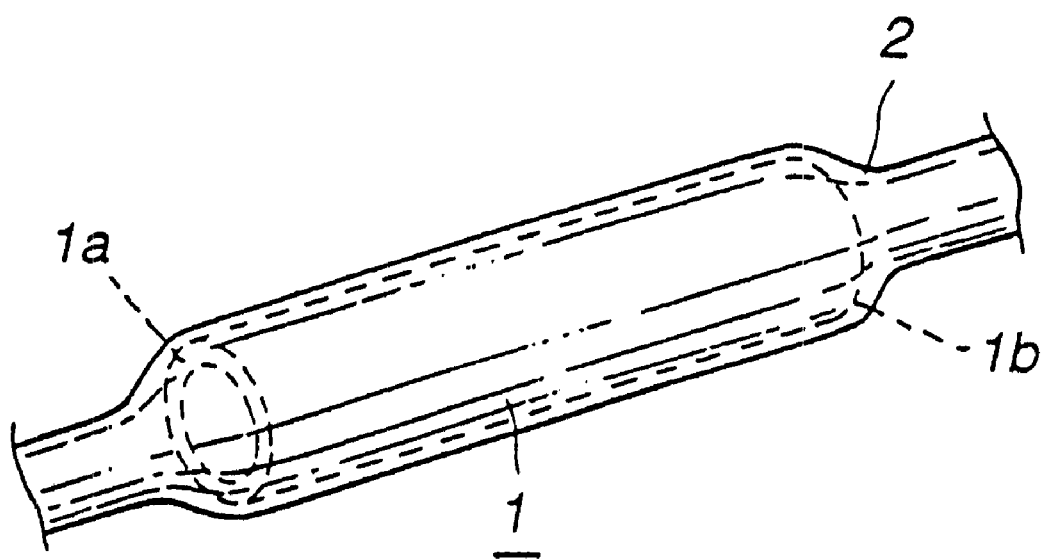
FIG. 11 is a perspective view showing the state in which a conventional stent for a vessel has been inserted into the blood vessel.

It is also possible to vary the cross-sectional shape of the fine metal wire or yarn of the main mid portion 34 and that of the fine metal wire or yarn of the ends of the tubular member 33 to form the low tenacity portions 35, 36 at the ends of the tubular member 33. That is, by flattening the cross-sectional shape of the fine metal wire or yarn of the ends of the tubular member 33, for example, it is possible to lower the tenacity thereat. Alternatively, the cross-sectional shape of the fine metal wire 32 or the yarn 42 making up the main mid portion 34 of the tubular member 33 may be set to an H-shape, as shown in FIG. 10, for increasing the tenacity of the fine metal wire 32 or the yarn 42 making up the main mid portion 34 over that of the fine metal wire or yarn making up the ends of the tubular member 33.

It is also possible to decrease the number of the fine metal wire or yarn from the main mid portion 34 towards the ends of the tubular member 33, in order to form the low tenacity portions 35, 36 at the respective ends of the tubular member 33 when preparing the tubular member 33 by knitting from the metal fine wires r polymer yarn.

The stent according to the present invention can be used not only for the blood vessel but also for other vessels of a living body, such as lymphoduct, bile duct or urinary duct.

INDUSTRIAL APPLICABILITY

With the stent for the vessel according to the present invention, in which low tenacity portions are formed integrally on both ends of the main mid portion, the vessel can be reliably maintained in an expanded state, while the stress-concentrated portions can be prevented from being produced in the vessel. It is thus possible with the stent for the vessel according to the present invention to prevent inflammation or excess thickening of the vessel and hence re-constriction in the vessel.

What is claimed is:

1. A stent for a vessel, inserted in use into the vessel of a living body, comprising:

a tubular member constituting a passageway from one end to the opposite end thereof;

said tubular member including a main mid portion formed by knitting a fine metal wire in a mesh shape, and low tenacity portions formed by polymer material and integrally with both ends of said main mid portion; said low tenacity portions being lower in tenacity than said main mid portion.

2. The stent for the vessel according to claim 1 wherein said tubular member includes the main mid portion having a defined mesh density and low density portions formed on both of the main mid portion by reducing the density of the meshes as compared to the of the main mid portion.

3. The stent for the vessel according to claim 1 wherein said tubular member includes the main mid portion formed by knitting the fine metal wire in meshes and low tenacity portions formed on both ends of said main mid portion in continuation with the main mid portion knitting a polymer fiber in a tubular form.

4. A stent for a vessel, inserted in use into the vessel of a living body, comprising:

a tubular member constituting a passageway from one end to the opposite end thereof;

said tubular member including a main mid portion formed by knitting a polymer yarn exhibiting biological absorptivity in a tubular shape, and low tenacity portions formed integrally with both ends of said main mid portion; said low tenacity portions being lower in tenacity than said main mid portion.

5. The stent for the vessel according to claim 4 wherein said tubular member includes the main mid portion having a defined mesh density and low density portions formed on both ends of the main mid portion by reducing the density of the meshes as compared to that of the main mid portion.

6. The stent for the vessel according to claim 4 wherein the polymer yarn is formed of a biologically absorptive polymer.

* * * * *